(12) United States Patent
Cohen et al.

(10) Patent No.: US 7,148,396 B2
(45) Date of Patent: Dec. 12, 2006

(54) DISPOSABLE GARMENT WITH SYSTEM FOR REDUCING HUMIDITY

(75) Inventors: Jason C. Cohen, Appleton, WI (US); Thomas Odorzynski, Green Bay, WI (US); Earl David Brock, Appleton, WI (US); Stephen E. Baldwin, Boise, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/941,367

(22) Filed: Sep. 15, 2004

(65) Prior Publication Data

US 2006/0058763 A1   Mar. 16, 2006

(51) Int. Cl.
*A61F 13/15* (2006.01)
*A61F 13/84* (2006.01)

(52) U.S. Cl. .................. 604/367; 604/360; 604/385.01

(58) Field of Classification Search ........ 604/360–361, 604/367, 358, 385.01, 385.101, 372, 378, 604/364

See application file for complete search history.

(56) References Cited

U.S. PATENT DOCUMENTS

| | | | |
|---|---|---|---|
| 4,381,782 A | 5/1983 | Mazurak et al. | |
| 4,749,392 A | 6/1988 | Aoki et al. | |
| 4,798,603 A | 1/1989 | Meyer et al. | |
| 5,092,008 A | 3/1992 | Okubo | |
| 5,176,668 A | 1/1993 | Bernardin | |
| 5,176,672 A | 1/1993 | Bruemmer et al. | |
| 5,192,606 A | 3/1993 | Proxmire et al. | |
| 5,356,678 A * | 10/1994 | Heitzhaus et al. | 428/35.6 |
| 5,509,915 A | 4/1996 | Hanson et al. | |
| 5,637,105 A | 6/1997 | Tanaka et al. | |
| 5,713,372 A | 2/1998 | Pinney et al. | |
| 5,773,105 A * | 6/1998 | Klett | 428/34.7 |
| 5,814,035 A * | 9/1998 | Gryskiewicz et al. | 604/385.21 |
| 5,843,056 A | 12/1998 | Good et al. | |
| 5,855,999 A | 1/1999 | McCormack | |
| 5,879,341 A | 3/1999 | Odorzynski et al. | |
| 5,907,908 A | 6/1999 | Cunanan et al. | |
| 5,935,304 A | 8/1999 | Shelley et al. | |
| 6,107,537 A | 8/2000 | Elder et al. | |
| 6,149,636 A * | 11/2000 | Roe et al. | 604/361 |
| 6,149,934 A | 11/2000 | Krzysik et al. | |
| 6,152,906 A * | 11/2000 | Faulks et al. | 604/385.01 |
| 6,153,209 A | 11/2000 | Vega et al. | |

(Continued)

FOREIGN PATENT DOCUMENTS

FR        2 578 444 A1        3/1985

(Continued)

OTHER PUBLICATIONS

International Search Report for PCT/US2005/020460 dated Sep. 9, 2005, 4 pages.

*Primary Examiner*—Tatyana Zalukaeva
*Assistant Examiner*—Laura C. Hill
(74) *Attorney, Agent, or Firm*—Senniger Powers

(57) ABSTRACT

A disposable garment generally has a liner, an outer cover, and a system for removing water vapor from an environment adjacent the wearer of the garment. A vapor permeable first container of the system contains a humidity reducing agent whereby the presence of humid air and the humidity reducing agent in the first container results in a liquid solution being formed therein. A second container of the system is in fluid communication with the first container for receiving liquid solution formed in the first container. The second container is at least in part liquid impermeable to retain therein liquid solution received from the first container.

35 Claims, 8 Drawing Sheets

U.S. PATENT DOCUMENTS

| | | | |
|---|---|---|---|
| 6,207,013 B1 | 3/2001 | Oriaran et al. | |
| 6,215,038 B1 | 4/2001 | Davis et al. | |
| 6,217,890 B1 | 4/2001 | Paul et al. | |
| 6,225,524 B1 | 5/2001 | Guarracino et al. | |
| 6,270,487 B1 | 8/2001 | Sheehan et al. | |
| 6,273,942 B1 | 8/2001 | Jersby | |
| 6,281,407 B1 | 8/2001 | Warner et al. | |
| 6,287,581 B1 * | 9/2001 | Krzysik et al. | 424/402 |
| 6,316,687 B1 * | 11/2001 | Davis et al. | 604/385.01 |
| 6,428,522 B1 | 8/2002 | DiPalma et al. | |
| 6,475,197 B1 | 11/2002 | Krzysik et al. | |
| 6,485,733 B1 | 11/2002 | Huard et al. | |
| 6,534,074 B1 | 3/2003 | Krzysik et al. | |
| 6,551,295 B1 | 4/2003 | Schmidt et al. | |
| 6,559,096 B1 | 5/2003 | Smith et al. | |
| 6,570,054 B1 | 5/2003 | Gatto et al. | |
| 6,613,029 B1 | 9/2003 | Kaylor et al. | |
| 6,652,775 B1 | 11/2003 | Payne et al. | |
| 6,845,513 B1 * | 1/2005 | Field et al. | 2/2.5 |
| 2001/0014350 A1 | 8/2001 | Krzysik et al. | |
| 2002/0006483 A1 * | 1/2002 | Neteler | 428/35.2 |
| 2002/0120242 A1 * | 8/2002 | Tyrrell et al. | 604/364 |
| 2002/0165508 A1 * | 11/2002 | Klofta et al. | 604/364 |
| 2003/0077962 A1 | 4/2003 | Krzysik et al. | |
| 2003/0130636 A1 | 7/2003 | Brock et al. | |

FOREIGN PATENT DOCUMENTS

| | | |
|---|---|---|
| FR | 2 750 618 A1 | 9/1998 |
| GB | 2 098 501 A1 | 11/1982 |
| GB | 2308814 A * | 7/1997 |
| JP | 4006047 A | 1/1992 |
| JP | 5068843 A | 3/1993 |
| WO | WO 96/40029 A1 | 12/1996 |
| WO | WO 9640029 A1 * | 12/1996 |
| WO | WO 00/72891 A1 | 12/2000 |
| WO | WO 00/72891 A1 * | 12/2000 |

* cited by examiner

DISPOSABLE GARMENT WITH SYSTEM FOR REDUCING HUMIDITY

BACKGROUND OF THE INVENTION

This invention relates generally to a disposable garment for personal wear, and more particularly to such a disposable garment that has a system for reducing humidity of the environment adjacent a wearer of the garment.

Disposable garments conventionally include garments worn like underpants for children and adults, garments worn like training pants for toddlers and garments worn like diapers for infants. Disposable absorbent garments designed to absorb and contain bodily fluids may include adult/child incontinence garments, toddler training pants and infant diapers. "Disposable" is generally understood to mean something that has a limited period of use before its ability to perform its intended function is exhausted. With regard to garments, "disposable" garments typically are not constructed to withstand laundering.

Disposable absorbent garments typically include a liquid permeable bodyside liner, a liquid impermeable outer cover, and an absorbent structure disposed between the bodyside liner and outer cover. To avoid leakage, the absorbent garment must rapidly take in liquid to avoid excessive pooling of liquid on the body-facing surface of the bodyside liner. However, any liquid taken in and retained by the garment contributes to the overall relative humidity near the wearer's skin. High relative humidity in the environment that contacts the wearer's skin is one of the primary causes of diaper dermatitis, commonly known as diaper rash. Diaper dermatitis can afflict almost every infant at some point in time during the diaper wearing years.

It is known to make the outer cover of the absorbent garment from a breathable material that is permeable to water vapor so that fresh air from outside the garment may replace the high humidity air in the environment near the wearer's skin. Also, it is known to incorporate humidity reducing agents (e.g., desiccants and/or humectants) into components of the diaper to reduce the relative humidity of the environment adjacent the skin of a wearer. The use of breathable outer covers and humidity reducing agents in components of the diaper has been effective at reducing relative humidity in the diaper and diaper dermatitis.

The addition of a disposable absorbent garment that effectively further reduces the relative humidity of the air near the skin of the wearer to further improve the skin health of the wearer is presented herein.

SUMMARY OF THE INVENTION

In one embodiment, a disposable garment of the present invention generally has a longitudinal direction, a lateral direction, a front waist region, a back waist region, a crotch region extending longitudinally between and interconnecting the front waist region and the back waist region, longitudinal ends, and lateral side edges. The disposable garment generally comprises a liner having a bodyfacing surface for facing a wearer of the garment, an outer cover in opposed relationship with the liner, and a system for removing water vapor from an environment adjacent the wearer of the garment. The system comprises a vapor permeable first container containing a humidity reducing agent whereby the presence of humid air and the humidity reducing agent in the first container results in a liquid solution being formed therein, and a second container in fluid communication with the first container for receiving liquid solution formed in the first container. The second container is at least in part liquid impermeable to retain therein liquid solution received from the first container.

In general, the present invention is also directed to a system for removing water vapor from an environment between an inner surface of a disposable absorbent garment and a wearer of the garment and retaining liquid solution in the disposable absorbent garment. The system comprises a vapor permeable first container for containing a humidity reducing agent in vapor communication with the environment whereby the presence of humid air and humidity reducing agent in the container results in a liquid solution being formed therein. A vapor permeable and liquid impermeable second container in fluid communication with the first container receives and retains liquid solution formed in the first container.

In another embodiment of the invention, the disposable absorbent garment has a longitudinal direction, a lateral direction, a front waist region, a back waist region, a crotch region extending longitudinally between and interconnecting the front waist region and the back waist region, longitudinal ends, and lateral side edges. The disposable absorbent garment generally comprises a liner having a bodyfacing surface for facing a wearer of the garment, an outer cover in opposed relationship with the liner, and an absorbent structure disposed between the liner and the outer cover for receiving liquid body waste that passes through the liner. A container is constructed of a vapor permeable material and contains a humidity reducing agent whereby the presence of humid air and the humidity reducing agent in the container results in a liquid solution being formed therein. The container is adapted to release liquid solution formed therein for flow to the absorbent structure.

Other features of the invention will be in part apparent and in part pointed out hereinafter

BRIEF DESCRIPTION OF THE DRAWINGS

Corresponding reference characters indicate corresponding parts throughout the several views of the drawings.

DETAILED DESCRIPTION OF THE INVENTION

The disposable garments of the present invention will be described herein with particular reference to a disposable absorbent garment, and more particularly to, a disposable diaper 20 adapted to be worn by infants or toddlers about the lower torso. It is understood, however, that the features of the present invention are equally adaptable to other types of disposable absorbent garments such as adult incontinence garments, training pants, disposable swim pants and feminine hygiene garments.

Figure 1:
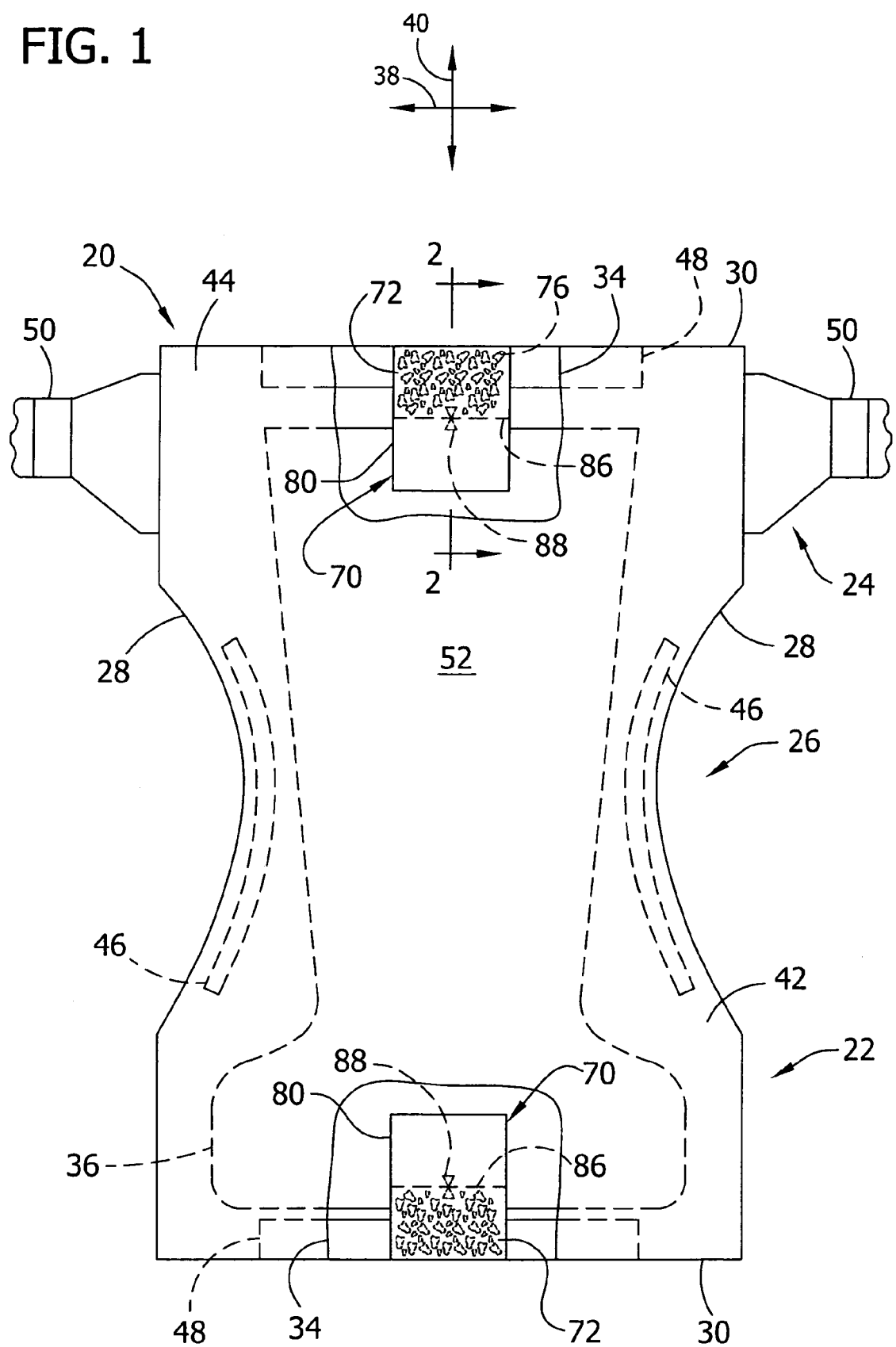
FIG. 1 is a top plan view of an absorbent garment of the present invention in a stretched and laid flat condition with the surface of the garment which contacts the skin of the wearer facing the viewer and with portions cut away to reveal internal construction.
Figure 2:
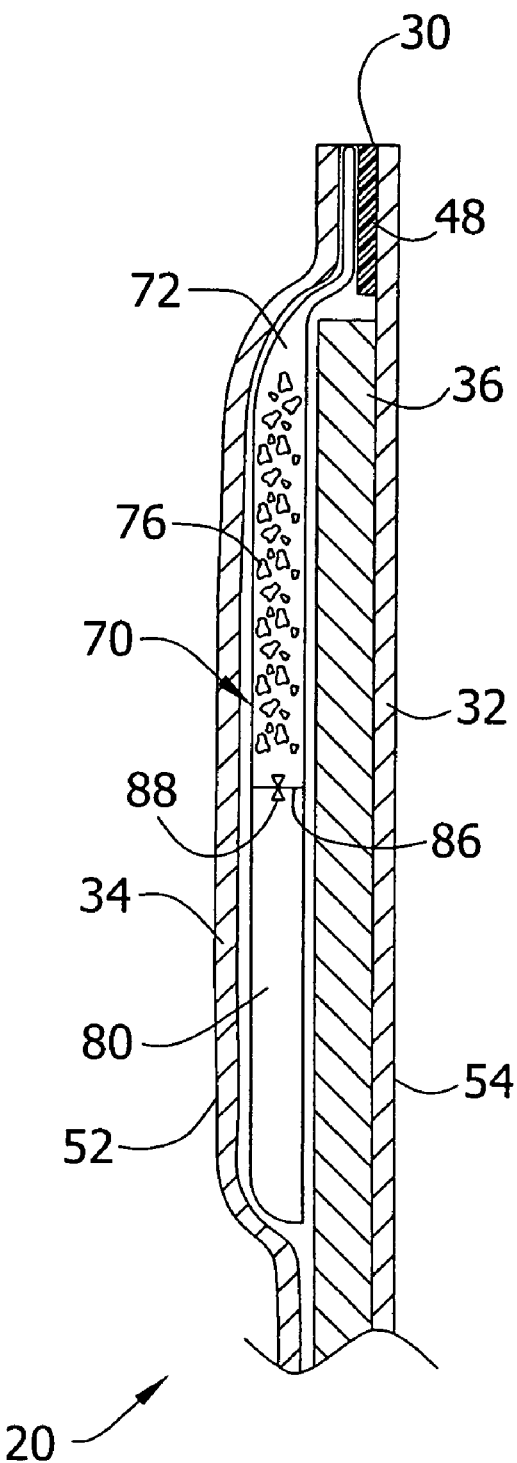
FIG. 2 is a partial cross-section taken along the plane including lines 2—2 in FIG. 1.

With reference to FIGS. 1 and 2 the disposable diaper 20 generally has a front waist region 22, a rear waist region 24, and a center region, otherwise referred to herein as a crotch region 26, extending longitudinally between and interconnecting the front and back waist regions 22, 24. The diaper 20 also has an inner surface 52 adapted in use (e.g., positioned relative to the other components of the diaper) to face the wearer, and an outer surface 54. The front and back waist regions 22, 24 comprise those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. With additional reference to FIG. 1, the diaper 20 has a pair of laterally opposite side edges 28, and a pair of longitudinally opposite end edges 30. The side edges 28 define leg openings for the diaper 20 and generally are curvilinear or contoured to more closely fit the legs of the wearer. The end edges 30 define a waist opening for the diaper 20 and typically are straight but may also be curvilinear.

The diaper 20 comprises a substantially liquid impermeable outer cover 32, a liquid permeable bodyside liner 34 positioned in facing relation with the outer cover 32, and an absorbent body or structure 36, such as an absorbent pad, which is located between the outer cover and the bodyside liner. The diaper 20 has a longitudinal direction 40 and a lateral direction 38 thereof perpendicular to the longitudinal direction as shown in FIG. 1. Marginal portions of the diaper 20, such as marginal sections of the outer cover 32, may extend beyond the terminal edges of the absorbent body 36. In the illustrated embodiment, for example, the outer cover 32 extends outwardly beyond the terminal marginal edges of the absorbent body 36 to form side margins 42 and end margins 44 of the diaper 20. The bodyside liner 34 has a bodyfacing surface and is generally coextensive with the outer cover 32, but may optionally cover an area that is larger or smaller than the area of the outer cover 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics 48 are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIG. 1, the elastic members 46 and 48 are illustrated in their uncontracted, stretched condition for the purpose of clarity. The diaper 20 may also include a pair of elasticized, longitudinally extending containment flaps (not shown), which are configured to maintain an upright, perpendicular arrangement in at least the crotch region 26 of the diaper to serve as an additional barrier to the lateral flow of body exudates. Suitable constructions and arrangements of containment flaps are well known to those skilled in the art.

Alternatively, the diaper 20 may include a pair of separate, elasticized and gathered leg gussets (not shown) or combination leg gussets/containment flaps (not shown) which are attached to the diaper along the side margins 42 in at least the crotch region 26 of the diaper 20 to provide elasticized leg cuffs. Such gussets or combination gussets/containment flaps may be configured to extend beyond and bridge across the respective concave portion of the side margins 42.

The diaper 20, as representatively illustrated in FIG. 1, may further include a pair of fasteners 50 employed to secure the diaper about the waist of a wearer. Suitable fasteners 50 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction 38 of diaper 20.

The diaper 20 may further include a surge management layer (not shown), positioned between the bodyside liner 34 and the absorbent body 36, configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of surge management layers are well known to those skilled in the art. Other suitable diaper components may also be incorporated on absorbent garments described herein.

The diaper 20 may be of various suitable shapes. For example, the diaper may have an overall rectangular shape, T-shape, or an approximately hour-glass shape. In the shown embodiment, the diaper 20 is I-shaped. Examples of diaper configurations suitable for use in connection with the instant application and other diaper components suitable for use on diaper 20 are described in U.S. Pat. No. 4,798,603 issued Jan. 17, 1989 to Meyer et al.; U.S. Pat. No. 5,176,668 issued Jan. 5, 1993, to Bernardin; U.S. Pat. No. 5,176,672 issued Jan. 5, 1993 to Bruemmer et al.; U.S. Pat. No. 5,192,606 issued Mar. 9, 1993 to Proxmire et al.; and U.S. Pat. No. 5,509,915 issued Apr. 23, 1996 to Hanson et al., the disclosures of which are hereby incorporated by reference. The various aspects and configuration of the invention can provide distinctive combinations of softness, body conformity, reduced red-marking of the wearer's skin, reduced hydration, and improved containment of body exudates.

The various components of the diaper 20 are assembled together using various suitable attachment means, such as adhesive, ultrasonic bonds, pressure bonds, thermal bonds, or combinations thereof. In the shown embodiment, for example, the bodyside liner 34 and the outer cover 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 by employing the above-identified attachment mechanisms.

The outer cover 32 of the diaper 20, as representatively illustrated in FIGS. 1 and 2, may suitably be composed of material which is either liquid permeable or liquid impermeable. It is generally preferred that the outer cover 32 be formed from a material which is substantially impermeable to liquids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mils) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art. Further, the outer cover 32 may be formed of a woven or nonwoven fibrous web layer which has been totally or partially constructed or treated to impart a desired level of liquid impermeability to selected regions that are adjacent or proximate to the absorbent body 36.

Desirably, the outer cover 32 may be composed of a "breathable" material which permits vapors to escape from the absorbent body 36 while still preventing liquid exudates from passing through the outer cover 32. For example, the outer cover 20 is desirably constructed to be permeable to at least water vapor and has a water vapor transmission rate (WVTR) of at least about 1000 $g/m^2/24$ hours, desirably at least about 1500 $g/m^2/24$ hours, more desirably at least about 2000 $g/m^2/24$ hours, and even more desirably at least about 3000 $g/m^2/24$ hours. Materials which have a water vapor transmission rate less than those above do not allow a sufficient amount of air exchange and undesirably result in increased levels of skin hydration. A suitable technique for determining the WVTR value of a material is the test procedure standardized by INDA (Association of the Nonwoven Fabrics Industry), number IST-70.4-99, which is incorporated by reference herein. The testing device which may be used for WVTR measurement is known as the Permatran-W Model 100K manufactured by Mocon/Modern Controls, Inc., with an office in Minneapolis, Minn.

In a particular embodiment, the outer cover 20 comprises a microporous film/nonwoven laminate material comprising a spunbond nonwoven material laminated to a microporous film. For example, the laminate may include a 0.6 osy (20.4 gsm) polypropylene spunbond material thermally attached to an 18.7 gsm stretched microporous film. The film may include from about 20 percent to about 75 percent by weight calcium carbonate particulates and the remainder primarily low density polyethylene. The film is then stretched which causes the polyethylene component to stretch while the particulates remain unstretched, thus causing voids to develop around the calcium carbonate particles in the film. The resulting laminate may define a water vapor transmission rate of from about 1000 to about 5000 $g/m^2/24$ hours.

Examples of suitable breathable materials for the outer cover 20 are also described in U.S. Pat. No. 5,879,341 issued Mar. 9, 1999 to Odorzynski et al. and entitled "ABSORBENT ARTICLE HAVING A BREATHABILITY GRADIENT"; U.S. Pat. No. 5,843,056 issued Dec. 1, 1988, to Good et al. and entitled ABSORBENT ARTICLE HAVING A COMPOSITE BREATHABLE OUTER COVER"; and U.S. Pat. No. 5,855,999 issued Jan. 5, 1999 to McCormack et al. and entitled "BREATHABLE, CLOTH-LIKE FILM/NONWOVEN COMPOSITE", the disclosures of which are herein incorporated by reference.

The absorbent body 36 of the diaper 20, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. An example of high-absorbency material suitable for use in the present invention is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body 36 in an amount of from about 5 to about 90 weight percent based on a total weight of the absorbent body.

Optionally, a substantially hydrophilic tissue wrapsheet (not shown) may be employed to help maintain the integrity of the airlaid fibrous structure of the absorbent body 36. The tissue wrapsheet is typically placed about the absorbent body 36 over at least the two major facing surfaces thereof and is composed of an absorbent cellulosic material, such as creped wadding or a high wet-strength tissue. In one aspect of the invention, the tissue wrapsheet can be configured to provide a wicking layer, which helps to rapidly distribute liquid over the mass of absorbent fibers comprising the absorbent body 36. In another aspect of the invention, the wrapsheet material on one side of the absorbent fibrous mass may be bonded to the wrapsheet located on the opposite side of the fibrous mass.

The bodyside liner 34, as representatively illustrated in FIGS. 1 and 2, suitably presents a bodyfacing surface 52 of the diaper 20 which is compliant, soft feeling, and non-irritating to the wearer's skin. Further, the bodyside liner 34 may be less hydrophilic than the absorbent body 36, to present a relatively dry surface to the wearer, and may be sufficiently porous to be liquid permeable, permitting liquid to readily penetrate through its thickness. A suitable bodyside liner 34 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The bodyside liner 34 is suitably employed to help isolate the wearer's skin from liquids held in the absorbent body 36.

Various woven and nonwoven fabrics can be used for the bodyside liner 34. For example, the bodyside liner 34 may be composed of a meltblown or spunbonded web of polyolefin fibers. The bodyside liner 34 may also be a bonded-carded web composed of natural and/or synthetic fibers. The bodyside liner 34 may be composed of a substantially hydrophobic material, and the hydrophobic material may, optionally, be treated with a surfactant, a wetting agent, or otherwise processed to impart a desired level of wettability and hydrophilicity. The bodyside liner 34 may be an elastic material such that the liner is elastically stretchable in the lateral direction 38 and/or the longitudinal direction 40. The term "stretchable" as used herein may include materials that are extensible and materials that are elastic. Suitable elastically stretchable materials are disclosed in U.S. patent application Ser. No. 10/879,323 filed Jun. 29, 2004 and titled "DISPOSABLE GARMENT WITH STRETCHABEL ABSORBENT ASSEMBLY", the disclosure of which is hereby incorporated by reference.

In one particular embodiment, the bodyside liner 34 may comprise a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.3 weight percent of a surfactant mixture, which contains a mixture of AHCOVEL Base N-62 and GLUCOPOAN 220UP surfactant in a 3:1 ratio based on a total weight of the surfactant mixture. The ANCOVEL Base N-62 is purchased from Hodgson Textile Chemicals Inc., (Mount Holly, N.C.) and includes a blend of hydrogenated ethoxylated castor oil and sorbitan monooleate in a 55:45 weight ratio. The GLUCOPAN 220UP is purchased from Henkel Corporation and includes alkyl polyglycoside. The surfactant may be applied by any conventional means, such as spraying, printing, brush coating, or the like. The surfactant may be applied to the entire bodyside liner 34, or may be selectively applied to particular sections of the bodyside liner 34, such as the medial section along the longitudinal centerline of the diaper, to provide greater wettability of such sections.

The bodyside liner 34 may further include a lotion or treatment applied thereto that is configured to be transferred to the wearer's skin. Suitable compositions for application to the bodyside liner 34 are described in U.S. Pat. No. 6,149,934 that issued to Krzysik et al. on Nov. 21, 2000 and U.S. patent application Ser. No. 10/660,319 filed Sep. 11, 2003, the disclosures of which are hereby incorporated by reference.

As shown in FIGS. 1 and 2, the diaper 20 comprises a system, generally indicated at 70, for reducing the humidity of the environment adjacent the wearer of the diaper. In the illustrated embodiment, two systems 70 are shown, each located at a respective front and rear waist region 22, 24 of the diaper. Each system 70 comprises a first container 72 containing a humidity reducing agent 76 for removing water vapor from the environment near the skin of the wearer and a second container 80 in fluid communication with the first container 72. When high relative humidity air permeates into the first container 72 the humidity reducing agent 76 absorbs from the vapor and, once it is saturated, dissolves in the water it absorbed. The resultant liquid solution flows into the second container 80 for storage within the diaper. In this way, the system 70 reduces the relative humidity of the environment near the wearer resulting in improved skin health of the wearer.

As shown in FIGS. 1 and 2, each system 70 has a generally rectangular shape and extends from a respective longitudinal edge margin 30 towards the crotch region 26 of the diaper 20. In the illustrated embodiment each system 70 extends laterally across a portion of the respective front and back waist region 22, 24 of the diaper 20. It is understood, though, that each system 70 could extend across the entire waist region 22, 24 of the diaper 20 and remain within the scope of this embodiment.

In one embodiment, the first container 72 comprises a pouch of vapor permeable and liquid impermeable material so that water vapor may permeate the container while liquid (e.g., urine) is prevented from entering the container. It is understood that the first container 72 may be positioned in the diaper 20 to reduce the amount of contact with liquid (e.g., urine) and instead comprise a pouch of vapor permeable and liquid permeable material. In the illustrated embodiment, the humidity reducing agent 76 suitably comprises desiccant granules (e.g., calcium chloride). It is understood, however, that the humidity reducing agent 76 could comprise other desiccant materials (e.g., aluminum oxide), chemicals that act as a humectants (e.g., glycerin), or a combination of both desiccants and humectants without departing from the scope of the invention. U.S. Pat. No. 6,281,407, incorporated by reference herein, identifies other desiccants and humectants suitable for use in the present invention. In the illustrated embodiment, the desiccant 79 comprises calcium chloride that removes water vapor from the air and forms a liquid solution comprising the dissolved calcium chloride and water. It is understood that the desiccant 79 could comprise other chemicals or compounds known in the art that remove water vapor from air by hydration (e.g., calcium sulfate, magnesium perchlorate, magnesium oxide, magnesium sulfate, potassium carbonate, potassium hydroxide, sodium sulfate, sulfuric acid, zinc chloride, etc.). A sufficient amount of desiccant 79 should be used so as to reduce the relative humidity of the environment in contact with the wearer's skin to approximately 80% or below to improve the skin health of the wearer and reduce the risk of diaper rash.

The second container 80 suitably comprises a flexible pouch constructed of a liquid impermeable and vapor permeable material. In the particular illustrated embodiment of FIGS. 1 and 2, the storage container 80 is formed integrally with the first container 72 and is separated therefrom by a divider panel 86 having an opening and a one-way check valve 88 therein to provide fluid communication between the containers. In particular, the check valve 88 allows liquid that collects in the humidity reducing agent pouch 72 to flow into the liquid retention pouch 80 and prevents the reverse flow of liquid from the liquid retention pouch to the agent containing pouch. It is understood that the divider panel 86 is suitably liquid impermeable, but could be liquid permeable without check valve 88. Also the containers 72, 80 could be discrete containers as discussed later herein. In the illustrated embodiment, the humidity reducing agent pouch 72 of each system 70 is positioned generally adjacent a respective longitudinal end 30 of the diaper 20 so that when the diaper is worn each pouch is positioned generally above the corresponding liquid retention pouch 80 to allow condensate to flow via gravity through the check valve 88. One suitable check valve 88 is a ¼ inch (6 mm) diameter model V24320 check valve manufactured by Halkey-Roberts Corporation in St. Petersburg, Fla. It is understood that the check valve 88 may be replaced with a water permeable membrane, a film having valve-type openings (e.g., DRI-WEAVE material), or a film having a small opening between the pouches that allows a small amount of fluid to flow back to the humidity reducing agent pouch 72.

In one embodiment the breathable and liquid impermeable material from which the liquid retention pouch 80 and/or humidity reducing agent pouch 72 are constructed may be similar to that of the outer cover 32. For example, the system 70 may comprise a liquid retention pouch 80 and/or humidity reducing agent pouch 72 that comprise a thin plastic film (e.g., polyethylene film having a thickness of from about 0.012 millimeter (0.5 mil) to about 0.051 millimeter (2 mils). Alternatively, the system 70 could comprise any other flexible, vapor permeable, and liquid impermeable material as described above for use as the outer cover 32 of the diaper 20. For example, the humidity reducing agent pouch 72 could be made from breathable plastic, paper products, TYVEX type material, or any other suitable material. In a particular embodiment, the humidity reducing agent pouch 72 and the liquid retention pouch 80 of the system 70 are made from the same liquid impermeable and vapor permeable material. The humidity reducing agent pouch 72 and the liquid retention pouch 80 are desirably constructed to be permeable to at least water vapor and have a minimum water vapor transmission rate (WVTR) ranging from about 1000 $g/m^2/24$ hours to about 25,000 $g/m^2/24$ hours. However, it will be understood that the liquid retention pouch 80 of the system 70 could be made from a barrier material (e.g., polyethylene, MYLAR film, or other nonporous film) that is both liquid and vapor impermeable so that water vapor in the liquid retention pouch is inhibited against permeating out from the pouch and into the environment between the diaper 20 and the wearer. In another embodiment, the liquid retention pouch 80 may contain an absorbent material (e.g., silica gel) to absorb and retain liquid in the pouch.

As shown in FIG. 2, the humidity reducing agent pouch 72 and the liquid retention pouch 80 of the system 70 are located below the bodyside liner 34 of the diaper 20 between the absorbent structure 36 and the liner. This positioning of the system 70 in the diaper 20 prevents the pouches 72, 80 from contacting the wearer's skin. It will be understood that the system 70 may be permanently attached to any component or layer of the diaper 20 by any conventional attachment means (e.g., adhesive) or the system may be removably attached to any component or layer of the diaper.

Figure 3:
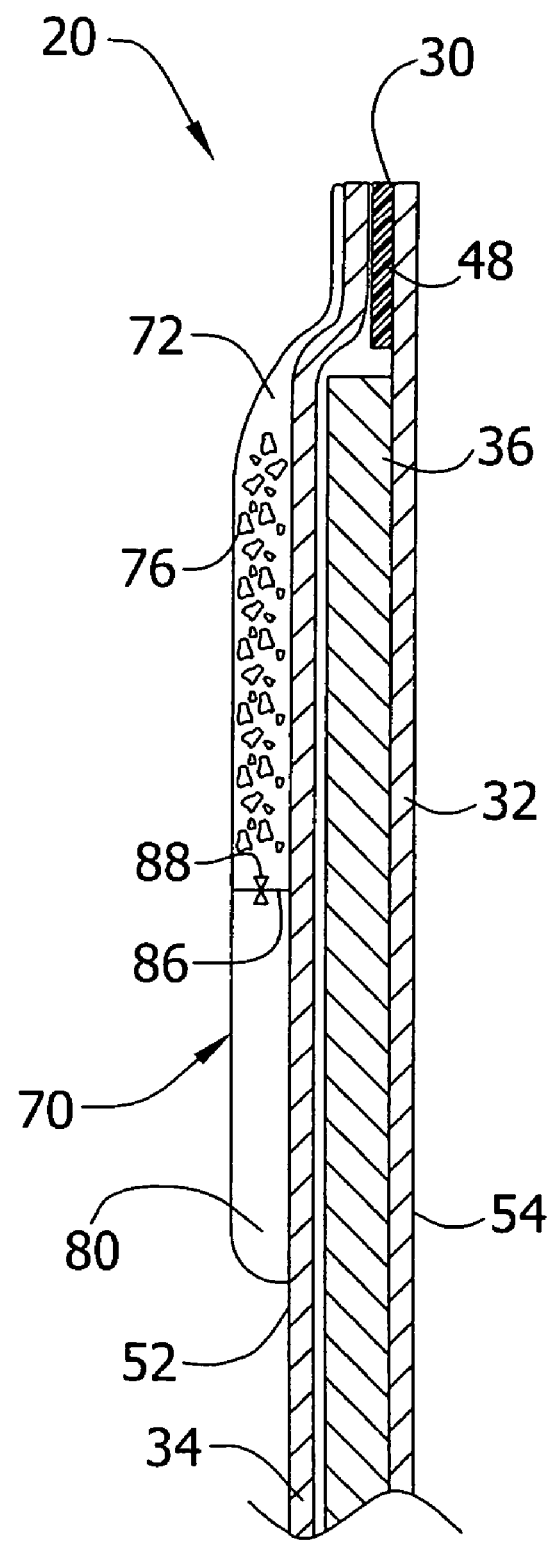
FIG. 3 is a view similar to FIG. 2 but showing a cross-section of an absorbent garment of a second embodiment of the invention.

FIG. 3 shows an alternative embodiment of the diaper 20 similar to the previous embodiment but with the system 70 positioned on the external surface 52 of the liner 34. In this embodiment, water vapor from the environment surrounding the wearer can enter the humidity reducing agent pouch 72 directly without having to permeate the liner 34 of the diaper 20. This positioning of the system 70 in the diaper 20 may lead to higher air flow into the humidity reducing agent pouch 72 and increased reduction in relative humidity of the environment adjacent the wearer's skin.

Figure 4:
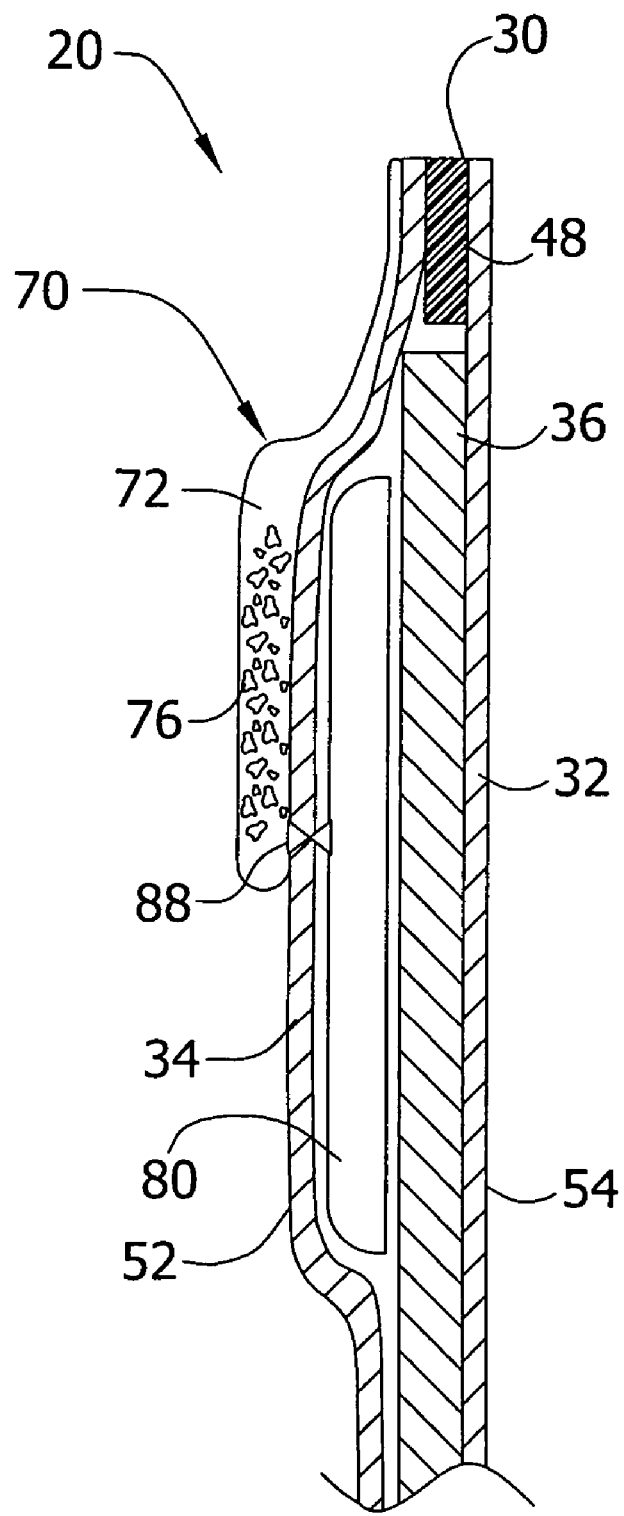
FIG. 4 is a view similar to FIG. 2 but showing a cross-section of an absorbent garment of a third embodiment of the invention.

FIG. 4 shows yet an alternative embodiment of the diaper 20 similar to the previous embodiments but with the system 70 comprising discrete first and second compartments. In particular, the first container comprises a humidity reducing agent pouch 72 positioned adjacent the external (e.g., body-facing) surface 52 of the liner 34 and the second container comprises a liquid retention pouch 80 positioned below the liner. Thus the humidity reducing agent pouch 72 and liquid retention pouch 80 are formed separately and positioned in separate layers of the diaper 20. The valve 88 extends through an opening in the liner 34 to allow fluid to pass from the humidity reducing agent pouch 72 through the liner into the liquid retention pouch 80 of the system 70. In this embodiment, only the humidity reducing agent pouch 72 of the system 70 is external to the liner 34 and exposed to the skin of the wearer as the liquid retention pouch 80 is located below the liner and protected from contact with the wearer's skin. It is understood that the liquid retention pouch 80 can be otherwise located in the diaper 20 without departing from the scope of this invention. For example, the liquid retention pouch 80 of the system 70 could be disposed between the absorbent structure 36 and the outer cover 32, or disposed between individual layers of a multi-layer outer cover.

Figure 5:
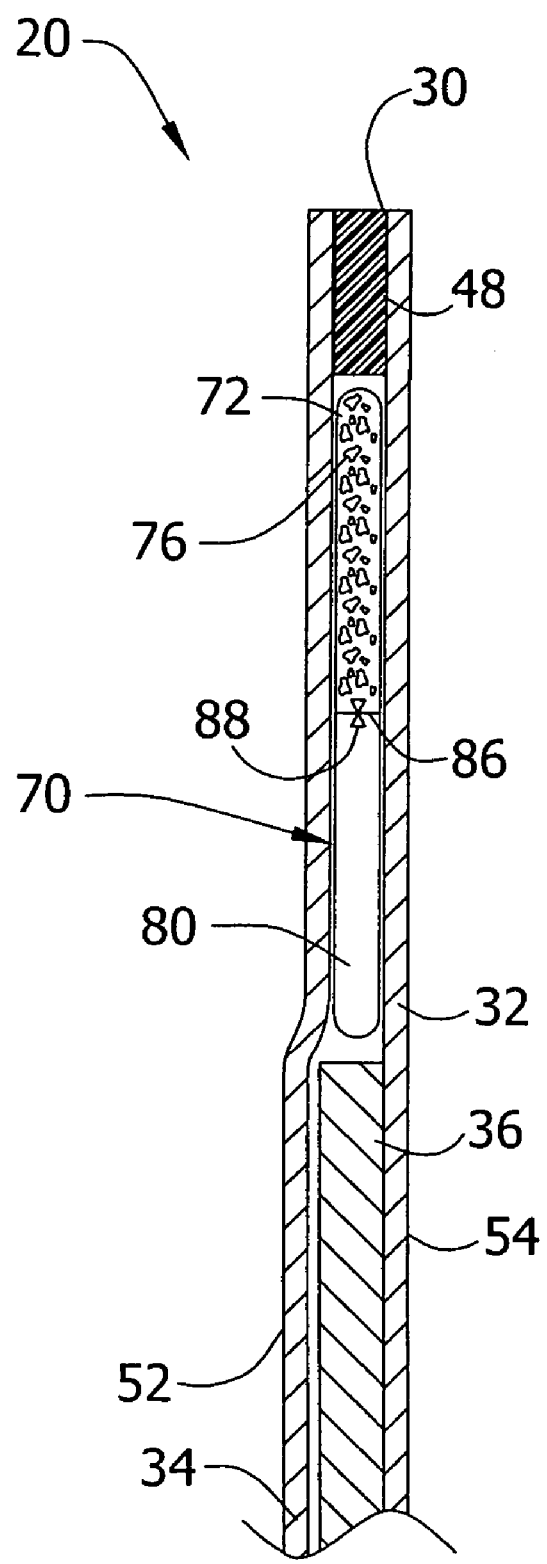
FIG. 5 is a view similar to FIG. 2 but showing a cross-section of an absorbent garment of a fourth embodiment of the invention.

FIG. 5 shows an alternative embodiment of the diaper 20 similar to the previous embodiments but having a system 70 comprising a humidity reducing agent pouch 72 (broadly, a first container) and liquid retention pouch 80 (broadly, a second container) that are integrally formed and disposed between the liner 34 and the outer cover 32. In this embodiment, the humidity reducing agent pouch 72 and liquid retention pouch 80 are located generally adjacent the longitudinal edge margins of the absorbent structure 36 in a portion of the diaper that is free of any intervening absorbent structure between the liner 34 and the outer cover 32. In this embodiment, the overall thickness of the waist band region of the diaper 20 that comprises the system 70 may be reduced to improve comfort and fit of the diaper.

Figure 6:
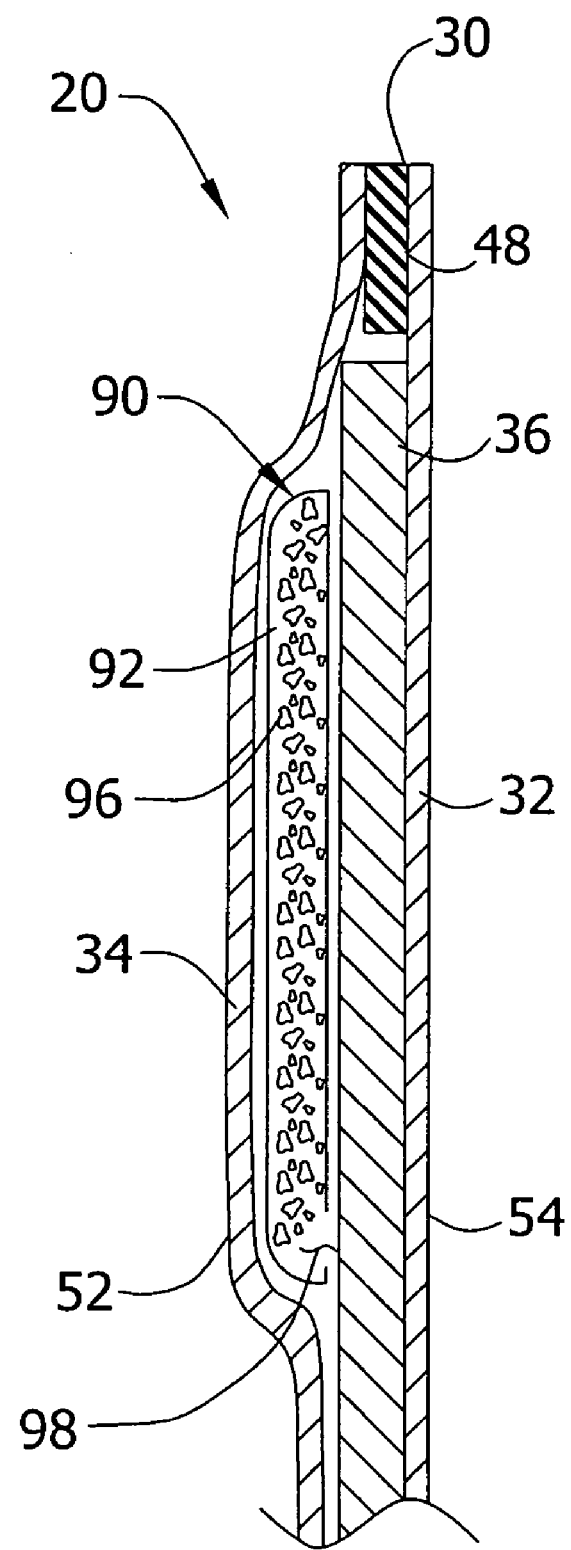
FIG. 6 is a view similar to FIG. 2 but showing a cross-section of an absorbent garment of a fifth embodiment of the invention.

FIG. 6 shows an alternative embodiment of the diaper 20 similar to the previous embodiments but having a system, generally indicated at 90, for removing water vapor from the environment adjacent the wearer of the diaper. In this embodiment, the system 90 comprises a single container in the form of a pouch 92 comprised of a liquid impermeable and vapor permeable material and containing humidity reducing agent 96. The single pouch 92 of the system 90 is disposed between the liner 34 and absorbent structure 36. The humidity reducing agent pouch 92 has an opening 98 that allows liquid solution formed in the pouch to flow directly into the absorbent structure 36 of the diaper 20. The opening 90 may comprise a patch of liquid permeable material that contains the desiccant 96 in the pouch 92 and allows fluid to flow into the absorbent structure 36 where it is stored in the diaper 20. Also, the opening 98 may comprise a check valve as described above to control the one-way flow of liquid solution from the desiccant pouch 90 to the absorbent structure 36.

Figure 7:
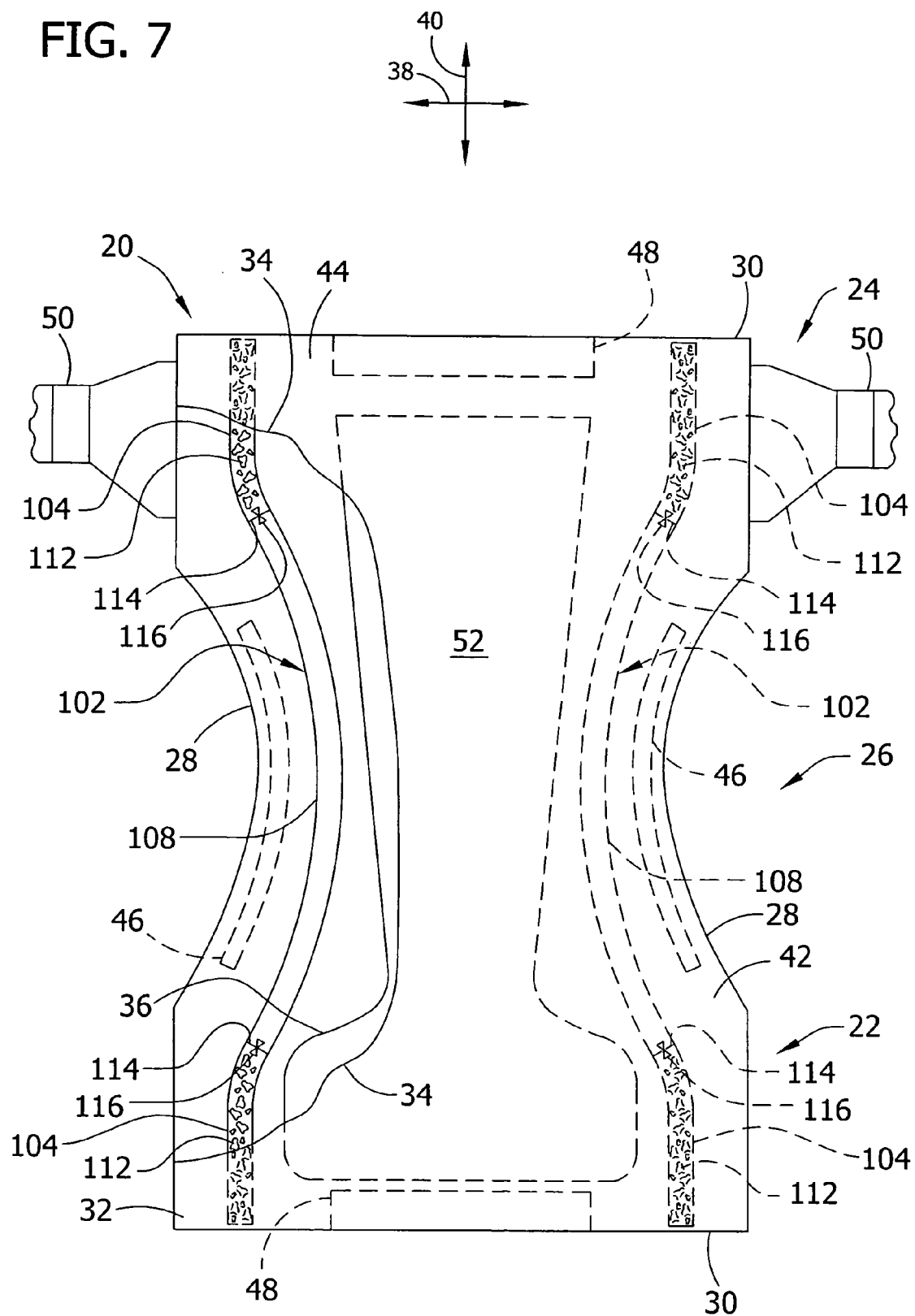
FIG. 7 is a top plan view of a sixth embodiment of the absorbent garment of the present invention shown in a stretched and laid flat condition with the surface of the garment which contacts the skin of the wearer facing the viewer and with portions cut away to reveal internal construction.

FIG. 7 shows an alternative embodiment of the diaper 20 similar to previous embodiments but having two systems, generally indicated 102, for removing water vapor from the environment adjacent the skin of the wearer in the form of tubes extending the length of the diaper 20. The tubes 102 extend in the longitudinal direction 40 from the front waist region 22, through the crotch region 26, to the back waist region 24 of the diaper 20. In the illustrated embodiment, the tubes 102 are located laterally between the leg elastic members 46 and the lateral side edges of the absorbent structure 36. Each tube 102 is located below the liner 34 but the tubes may be otherwise located (e.g., above the liner or below the absorbent structure 36) and one or more than two tubes may be located in the diaper 20 without departing from the scope of this invention.

Each tube 102 comprises a pair of humidity reducing agent containers, 104 (broadly, first container) generally near a respective longitudinal end 30 of the diaper 20 and a liquid retention container 108 (broadly, a second container) in the crotch region 26 of the diaper between the two humidity reducing agent containers. In the illustrated embodiment, the two humidity reducing agent containers 104 contain desiccant material 112 in the form of calcium chloride granules, but other desiccant or humectant material may be used. As with the previous embodiments, the humidity reducing agent container 104 comprises a vapor permeable and liquid impermeable material to allow water vapor from the environment surrounding the wearer of the diaper 20 to permeate the tube 102 and contact the desiccant material 112 contained therein.

The condensate container 108 of each system 102 is generally located in the crotch region 26 of the diaper 20 and is positioned to receive condensate from both the humidity reducing agent containers 104. As with the previous embodiments, the liquid retention container 108 may be separated from each humidity reducing agent container 104 by a divider panel 114 that comprises a check valve 116 to prevent fluid from flowing from the liquid retention container back into the humidity reducing agent containers. Also, the liquid retention container 108 may contain an absorbent material (e.g., silica gel or any other absorbent material known in the art) to absorb and retain condensate in the system 102. When the diaper 20 is attached to the wearer, the two humidity reducing agent containers 104 are located generally above the liquid retention container 108 so that condensate that collects in each humidity reducing agent container flows by gravity through the check valve 116 and into the liquid retention container.

Figure 8:
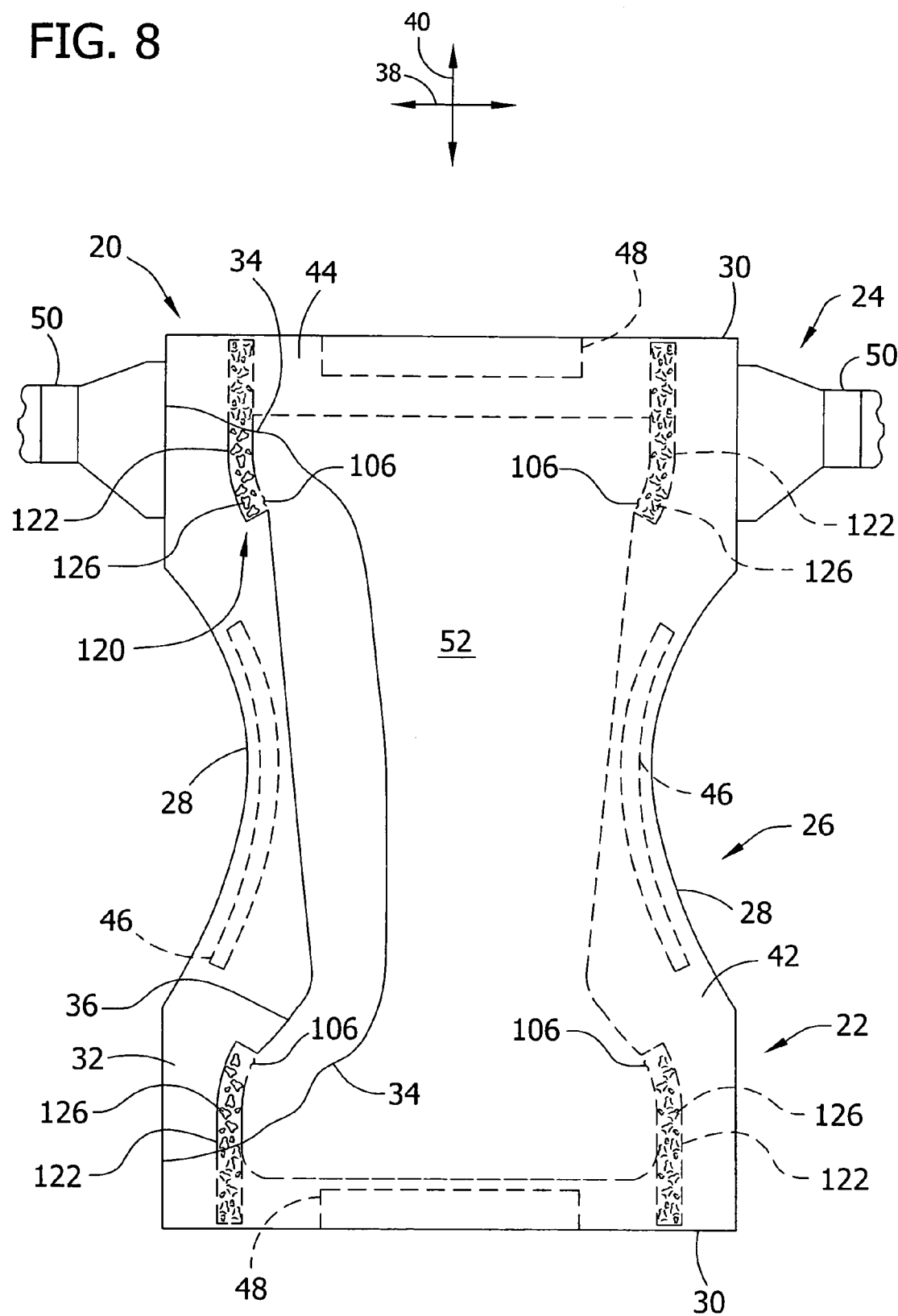
FIG. 8 is a view similar to FIG. 7 but showing an absorbent garment of a seventh embodiment of the present invention.

FIG. 8 shows an alternative embodiment of the diaper 20 similar to the embodiment of FIG. 7 but showing a system, generally indicated 120, comprising four tubes 122 (broadly, containers) each containing humidity reducing agent 126. One pair of tubes 122 are located generally adjacent the opposed lateral side edges of the absorbent structure 36 in the front waist region 22 of the diaper 20. A second pair of tubes 122 is located at the opposed lateral side edges of the absorbent structure 36 in the back waist region 24 of the diaper 20. Each tube 122 is located beneath the liner 34 and laterally between the lateral side edges 28 of the diaper 20 and the absorbent structure 36. Each tube 122 comprises a vapor permeable and liquid impermeable material and contains humidity reducing agent 126 in the form of a desiccant material that absorbs water from the water vapor and forms a liquid solution.

In the embodiment of FIG. 8 each tube 122 is adapted to drain directly into the absorbent structure 36 of the diaper 20 so that liquid solution that collects in the tube can flow into the absorbent structure for storage in the diaper. Each tube 122 comprises an opening 106 as described above for the previous embodiments to allow fluid to exit the liquid impermeable tube for storage in the absorbent structure 36. The opening 106 may have a check valve therein to prevent the backflow of liquid into the tube. The tubes 104 may be located in the diaper at any location that allows fluid to drain into the absorbent structure 36. Less than or more than four tubes 104 may be used in the diaper 20 and the tube(s) may extend longitudinally through the front waist region, crotch region, and/or back waist region of the diaper without departing from the scope of this invention.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. A disposable garment, the disposable garment having a longitudinal direction, a lateral direction, a front waist region, a back waist region and a crotch region extending longitudinally between and interconnecting the front waist region and the back waist region, longitudinal ends and lateral side edges, the disposable garment comprising:

a liner having a bodyfacing surface for facing a wearer of the garment;

an outer cover in opposed relationship with the liner;

a system for removing water vapor from an environment adjacent the wearer of the garment, the system comprising a first container containing a humidity reducing agent whereby the presence of humid air and the humidity reducing agent in the first container results in a liquid solution being formed therein, the first container being constructed at least in part of a vapor permeable and liquid impermeable material, and a second container in fluid communication with the first container for receiving liquid solution formed in the first container, the second container being at least in part liquid impermeable to retain therein liquid solution received from the first container.

2. The disposable garment set forth in claim 1 further comprising an absorbent structure disposed between the liner and the outer cover for receiving body waste that passes through the liner.

3. The disposable garment set forth in claim 1 wherein said first container and second container are integrally formed and separated by a divider panel.

4. The disposable garment set forth in claim 3 wherein said panel has an opening therein to permit the flow of liquid solution from the first container to the second container.

5. The disposable garment set forth in claim 3 wherein said divider panel is comprised at least in part of a liquid permeable material.

6. The disposable garment set forth in claim 4 wherein said system comprises a valve in the opening.

7. The disposable garment set forth in claim 1 wherein the system comprises a valve between the first and second containers to allow the flow of liquid solution from the first container to the second container and to prevent the flow of liquid solution from the second container to the first container.

8. The disposable garment set forth in claim 1 wherein the system is adapted for gravity flow of condensate from the first container to the second container.

9. The disposable garment set forth in claim 2 wherein the first and second containers are disposed between the absorbent structure and the liner.

10. The disposable garment set forth in claim 2 wherein the first container is in contact with the bodyfacing surface of the liner and the second container is disposed between the absorbent structure and the liner.

11. The disposable garment set forth in claim 9 wherein the first and second containers are each in contact with the bodyfacing surface of the liner.

12. The disposable garment set forth in claim 1 wherein said humidity reducing agent is a desiccant.

13. The disposable garment set forth in claim 12 wherein the desiccant comprises calcium chloride.

14. The disposable garment set forth in claim 1 wherein said humidity reducing agent is selected from the group consisting of calcium chloride, calcium sulfate, magnesium perchlorate, magnesium oxide, magnesium sulfate, potassium carbonate, potassium hydroxide, sodium sulfate, sulfuric acid, zinc chloride, and combinations thereof.

15. The disposable garment set forth in claim 1 wherein said first container and said second container are disposed in at least one of the front and back waist regions of the garment.

16. The disposable garment set forth in claim 1 wherein said system comprises a vapor permeable and liquid impermeable tube extending longitudinally from the front waist region of the garment to the back waist region of the garment, said tube comprising at least one first container containing a humidity reducing agent and at least one second container, said containers being separated by a divider panel within the tube.

17. A system for removing water vapor from an environment between an inner surface of a disposable absorbent garment and a wearer of the garment and retaining liquid solution in the disposable absorbent garment, the system comprising:

a vapor permeable first pouch for containing a humidity reducing agent in vapor communication with the environment whereby the presence of humid air and humidity reducing agent in the pouch results in a liquid solution being formed therein; and a vapor permeable and liquid impermeable second pouch in fluid communication with the first pouch for receiving and retaining liquid solution formed in the first pouch.

18. The system for removing water vapor set forth in claim 17 wherein the first pouch is constructed at least in part of a vapor permeable and liquid impermeable material.

19. The system for removing water vapor set forth in claim 17 wherein said first pouch and second pouch are integrally formed and separated by a divider panel.

20. The system for removing water vapor set forth in claim 17 wherein said panel has an opening therein to permit the flow of liquid solution from the first pouch to the second pouch.

21. The system for removing water vapor set forth in claim 20 wherein said divider panel is comprised at least in part of a liquid permeable material.

22. The system for removing water vapor set forth in claim 20 wherein said opening comprises a valve to control the flow of liquid solution between the first and second pouches.

23. The system for removing water vapor set forth in claim 17 further comprising a valve between the first and second pouches to allow the flow of liquid solution from the first pouch to the second pouch and to prevent the flow of liquid solution from the second pouch to the first pouch.

24. The system for removing water vapor set forth in claim 17 wherein said humidity reducing agent is a desiccant.

25. The system for removing water vapor set forth in claim 24 wherein said desiccant comprises calcium chloride.

26. The system for removing water vapor set forth in claim 17 wherein said humidity reducing agent is selected from the group consisting of calcium chloride, calcium sulfate, magnesium perchlorate, magnesium oxide, magnesium sulfate, potassium carbonate, potassium hydroxide, sodium sulfate, sulfuric acid, zinc chloride, and combinations thereof.

27. A disposable absorbent garment, the disposable absorbent garment having a longitudinal direction, a lateral direction, a thickness direction, a front waist region, a back waist region and a crotch region extending longitudinally between and interconnecting the front waist region and the back waist region, longitudinal ends and lateral side edges, the disposable absorbent garment comprising:

a liner having a bodyfacing surface for facing a wearer of the garment;

an outer cover in opposed relationship with the liner;

an absorbent structure disposed between the liner and the outer cover for receiving liquid body waste that passes through the liner; and a container separate from the liner and constructed of a vapor permeable and liquid impermeable material and containing a humidity reducing agent whereby the presence of humid air and the humidity reducing agent in the container results in a liquid solution being formed therein, the container being adapted to release liquid solution formed therein for flow to the absorbent structure, said container being disposed at least one of on the bodyfacing surface of the liner and intermediate the absorbent structure and the liner in the thickness direction of the garment.

28. The disposable absorbent garment set forth in claim 27 wherein said container has an opening therein to permit liquid solution formed in the container to flow out of the container to the absorbent structure.

29. The disposable absorbent garment set forth in claim 28 wherein said opening comprises a liquid permeable material.

30. The disposable absorbent garment set forth in claim 28 further comprising a check valve in the opening to prevent the flow of liquid through the opening into the container.

31. The disposable absorbent garment set forth in claim 27 wherein said humidity reducing agent is a desiccant.

32. The disposable absorbent garment set forth in claim 29 wherein said desiccant comprises calcium chloride.

33. The disposable absorbent garment set forth in claim 27 wherein said humidity reducing agent is selected from the group consisting of calcium chloride, calcium sulfate, magnesium perchlorate, magnesium oxide, magnesium sulfate, potassium carbonate, potassium hydroxide, sodium sulfate, sulfuric acid, zinc chloride, and combinations thereof.

34. The disposable garment set forth in claim 1 wherein the first and second containers are formed separate from the outer cover and the liner.

35. A disposable garment, the disposable garment having a longitudinal direction, a lateral direction, a front waist region, a back waist region and a crotch region extending longitudinally between and interconnecting the front waist region and the back waist region, longitudinal ends and lateral side edges, the disposable garment comprising:

a liner having a bodyfacing surface for facing a wearer of the garment;

an outer cover in opposed relationship with the liner;

a system for removing water vapor from an environment adjacent the wearer of the garment, the system comprising a vapor permeable first container containing a humidity reducing agent whereby the presence of humid air and the humidity reducing agent in the first container results in a liquid solution being formed therein, and a second container in fluid communication with the first container for receiving liquid solution formed in the first container, the second container being at least in part liquid impermeable to retain therein liquid solution received from the first container, the second container being at least in part longitudinally aligned with the first container and extending at least in part beyond the first container to facilitate the flow of liquid solution from the first container to the second container.

* * * * *